United States Patent [19]
Imai et al.

[11] Patent Number: 4,578,499
[45] Date of Patent: Mar. 25, 1986

[54] OXALIC ACID ESTER DERIVATIVES

[75] Inventors: Kazuhiro Imai; Hiroshi Ogata; Motoaki Tanaka, all of Tokyo; Hiroyoshi Nawa; Masami Ishihara, both of Saitama, all of Japan

[73] Assignee: Wako Pure Chemical Industries Ltd., Osaka, Japan

[21] Appl. No.: 749,428

[22] Filed: Jun. 27, 1985

[30] Foreign Application Priority Data

Jun. 30, 1984 [JP] Japan ................ 59-136060

[51] Int. Cl.⁴ .............................. C07C 79/46
[52] U.S. Cl. ...................... 560/21; 252/301.16; 252/700; 252/408.1; 435/183
[58] Field of Search ............ 560/21, 22, 146, 142, 560/138

[56] References Cited

U.S. PATENT DOCUMENTS

| | | | |
|---|---|---|---|
| 3,597,362 | 8/1971 | Bollyky et al. | 560/146 X |
| 3,704,309 | 11/1972 | Maulding | 560/146 X |
| 3,749,679 | 7/1973 | Rauhut | 560/146 X |
| 3,781,329 | 12/1973 | Bollyky et al. | 560/146 |
| 4,053,430 | 10/1977 | Mohan | 560/146 X |

Primary Examiner—Bernard Helfin
Attorney, Agent, or Firm—Cushman, Darby & Cushman

[57] ABSTRACT

Disclosure herein is novel oxalic acid ester derivatives represented by the general formula:

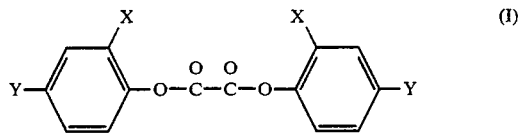

wherein either one of X and Y represents a nitro group, and the other represents

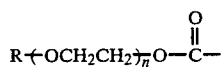

in which R represents a lower alkyl group, and n represents a figure of 1–50. The oxalic acid ester derivatives are useful as chemiluminescent reagents for fluororescent substances.

11 Claims, 1 Drawing Figure

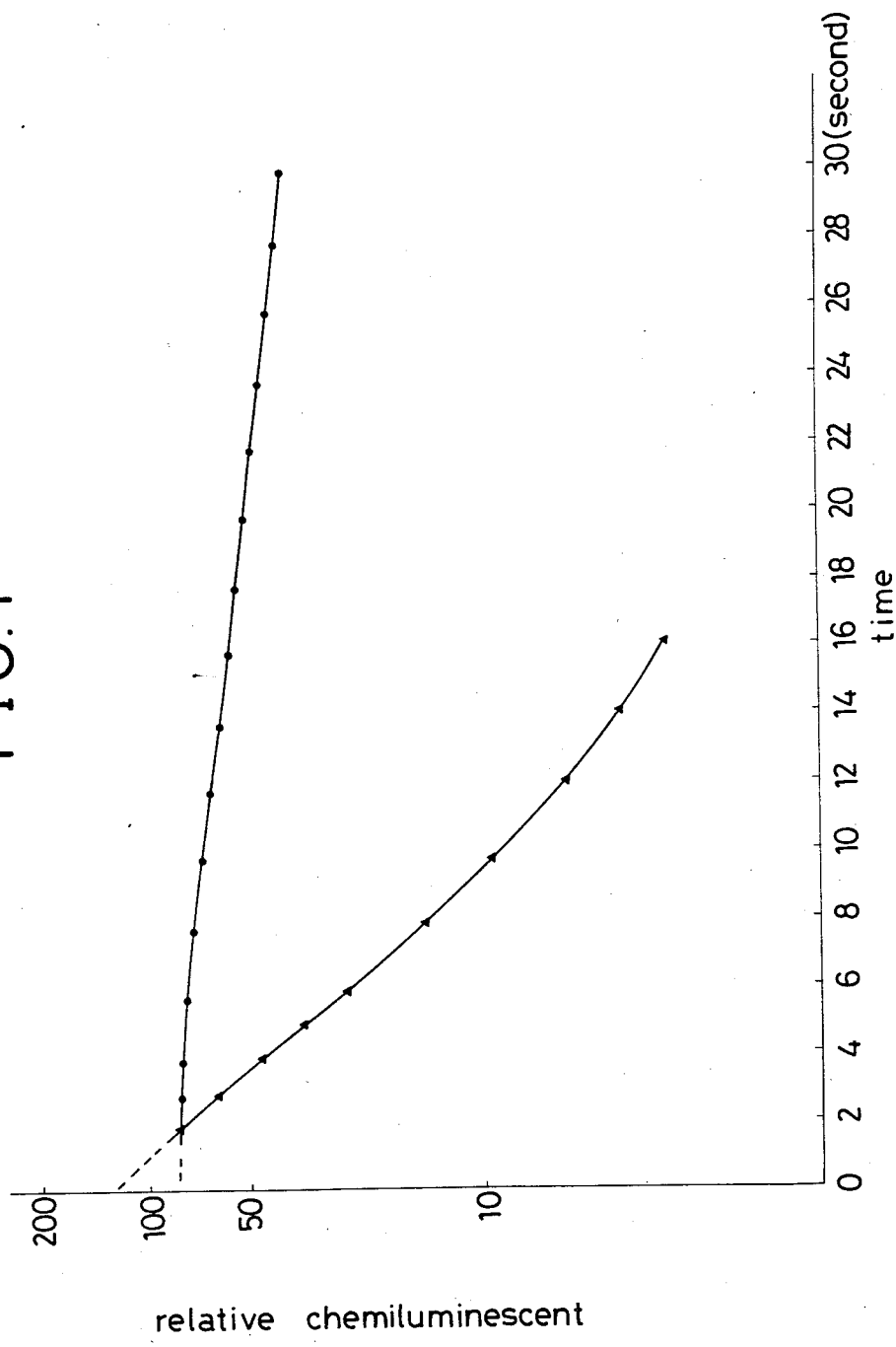

OXALIC ACID ESTER DERIVATIVES

BACKGROUND OF THE INVENTION (1) Field of the Invention

The present invention relates to novel oxalic acid ester derivatives useful for quantitatively measuring a small amount of fluorescent substances, and hydrogen peroxide itself or produced, for instance, in enzyme immuno assay.

(2) Description of the Prior Art

An active intermediate (1,2-dioxethanedione) which is formed by an oxalic acid ester and hydrogen peroxide excite the fluorescent substances and make emission thereof, although there may be difference in quantum yield, so long as the substances have fluorescence from the visible range to the infrared range. The reaction systems thereof is used for quantitative measurement of hydrogen peroxide, substances participating in enzymatic reactions to produce hydrogen peroxide, and the like. Further, the fluorescent substances as receptors for energy from the active intermediates can also be measured thereby. Moreover, these quantitative measurements have been adopted as a methods of quantitatively measuring with high sensitivity a very small amount of hydrogen peroxide produced, for instance, in enzyme immuno assay and a method of quantitatively measuring with high sensitivity a fluorescent substance through being subjected to a main reaction after separated by high performance liquid chromatography (HPLC).

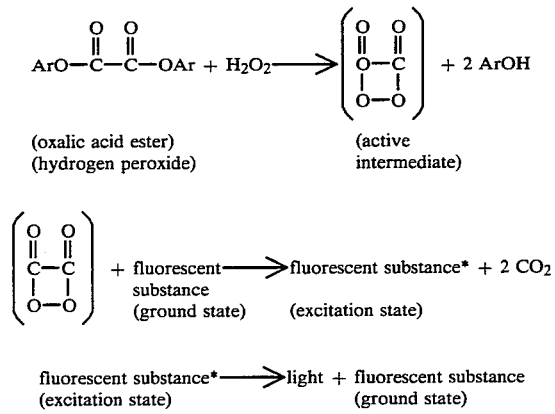

It is indispensable to obtain a reliable measured value by using a very small amount of a sample in the field in which diagnosis or treatment is performed through grasping the intracorporeal dynamics of a component of a living body, and the highly sensitive quantitatively measuring methods using the above reaction have been successively developed. For instance, there have been disclosed a quantitative measurement of hydrogen peroxide in the enzyme immunoassay of 17 α-hydroxyprogesterone [Arakawa et at., Chem. Pharm. Bull., 30, 3036, (1982)] and so on, quantitative measurements of urinary glucose [Williams et al., Anal. Chem., 48, 1003(1976)] and the activity of lactate dehydrogenase [Williams et al., Anal. Chem., 48, 1478(1976)], a quantitative measurement of dansylamino acid in HPLC [Kobayashi et al., Anal. Chem., 52, 424(1980)], a quantitative measurement of fluoresamine labeled cathecoalamine [Kobayashi et al., Anal. Biochem., 112, 99(1981)] and so on.

Among the chemiluminescent reagents giving the above high sensitive chemiluminescence, there are many compounds offered as the oxalic acid esters. For instance, use may be ordinarily made of bis(2,4,6-trichlorophenyl)-oxalate(hereinafter abbreviated as TCPO), bis(2,4-dinitrophenyl)oxalate(hereinafter abbreviated as DNPO), bis(pentachlorophenyl)oxalate, bis(4-nitro-3-trifluoromethyl)oxalate, bis(4-nitro-2-formylphenyl)-oxalate, bis(pentafluorophenyl)oxalate and so on.

However, there is no limit for needs in the scientific world, and the conventional chemiluminescent reagents have not been satisfactory in light of the requirements that sensitivity is higher; even when the oxalic acid esters is used at a high concentration, high emission intensity can be obtained without lowering the quantum yield; chemiluminescent life is still longer in a low chemiluminescent intensity system; the solubility to desired hydrophilic organic solvents is extremely high; and so forth. For instance, there has been offered DNPO as a chemiluminescent reagent with extremely excellent sensitivity [Rauhut et al., J. Amer. Chem. Soc., 89, 6515(1967)], but it was not satisfactory in terms of requirements other than the sensitivity, that is, this chemiluminescent substance has the defects that it does not have the stability required to be offered for the scientific world and the solubility to the hydrophilic organic solvents is low.

SUMMARY OF THE INVENTION

It is therefore an object of the present invention to provide novel and more effective oxalic acid ester derivatives for use in detecting hydrogen peroxide or fluorescent substances with higher sensitivity in the measurement of very small amount components in a body fluid or components in a living body, which exhibit physiological activity even in a small amount, through utilizing chemiluminescent reaction.

It is another object of the present invention to provide novel oxalic acid ester derivatives which are extremely high in the solubility to hydrophilic organic solvents.

It is still another object of the present invention to provide novel oxalic acid ester derivatives which have excellent stability and extremely long chemiluminescent life.

That is, according to the present invention, there is a provision of the oxalic acid ester derivatives represented by the general formula:

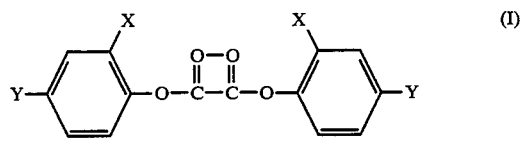

wherein either one of X and Y represents a nitro group, and the other represents

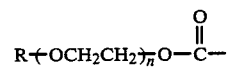

in which R represents a lower alkyl group and n represents a figure of 1–50.

These and other objects, features and advantages of the present invention will be well appreciated upon reading of the following description of the invention when taken in connection with the attached drawing with understanding that some modifications, variations and changes of the same could be easily done by the skilled in the art to which the invention pertains without departing from the spirit of the invention or the scope of claims appended hereto.

BRIEF DESCRIPTION OF THE DRAWING

For better understanding of the invention, reference is made of the attached drawing, wherein:

FIG. 1 shows changes in chemiluminescent intensity with lapse of time in regard to ECNPO as one of the compounds according to the present invention and a known DNPO in Example 6 by using a semi-logarithm graph in which the ordinate shows a relative chemiluminescent intensity and an abscissa does a time(second), provided that -●-●- and -▲-▲- show measured results with respect to ECNPO and DNPO, respectively, and a dotted line being an extrapolatory curve.

DETAILED DESCRIPTION OF THE INVENTION

Upon having made strenuous studies through repeated molecule construction and screening to meet the above-mentioned needs, the present inventors have reached compounds according to the present invention and accomplished the invention.

That is, the present invention relates to oxalic acid ester derivatives represented by the general formula:

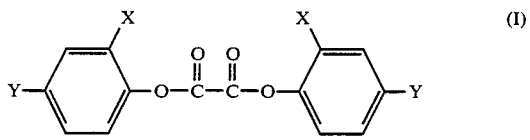  (I)

wherein either one of X and Y represents a nitro group, and the other represents

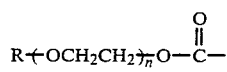

in which R represents a lower alkyl group and n represents a figure of 1-50.

Since the novel oxalic acid ester derivatives according to the present invention are extremely higher in solubility to hydrophilic organic solvents such as acetonitrile, acetone and so on suitable for the reaction with hydrogen peroxide in the measurement of a sample in a living body such as components in a body fluid, ethyl acetate and so on similarily used, as compared with the above-mentioned DNPO (see Table 1), when the derivatives of the invention are used as chemiluminescent reagents in the chemiluminescent reaction, they can be employed in a greater amount than DNPO, so that active intermediates are accordingly produced in a larger amount in the system, and consequently more extremely excellent chemiluminescent reaction can be attained. Further, the compounds according to the present invention are excellent in stability as chemiluminescent reagent, and have extremely long chemiluminescent life (see Table 1). Therefore, the compounds of the present invention can be more effectively used for quantitatively measuring hydrogen peroxide or substances participating in enzymatic reactions to produce hydrogen peroxide by using the chemiluminescent reaction.

These compounds can be also extremely effectively used for quantitatively measuring with high sensitivity a very small amount of hydrogen peroxide produced in the enzyme immunoassay. Furthermore, since the quantitative measurement of the fluorescent substance itself as a receptor for energy from the active intermediate, can be effected at higher sensitivity by using the compounds according to the present invention as chemiluminescent reagent in the chemiluminescent reaction, based on this, a very small amount of a component in a body fluid or a component in a living body which exhibits its physiological activity even in a small amount can be detected and quantitatively measured in an extremely highly sensitive and selective manner by separating by means of HPLC, a very small amount of an amino acid in blood of an infant or a cathecolamine such as dopamin (DA), noruepinephrine (NE), epinephrine (E) and so on which are present as physiologically active amine at a very low concentration in the body fluid and then performing the quantitative measurement thereof after labelling is carried out by using a fluorescent reagent such as NBD-F(7-fluoro-4-nitrobenzoxadiazole), dansylchloride, or fluoresamine.

In Table 1, the solubilities of some of the compounds according to the present invention to a few solvents are shown in comparison with those of DNPO. Figures in this Table each show amounts (magnification) of a solvent required to dissolve 50 mg of a sample at 2020 C.

TABLE 1

| compounds according to the invention of the formula: 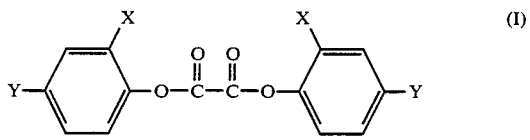 | Solubility | | |
|---|---|---|---|
| | acetonitrile times | acetone times | ethyl acetate times |
| (1) X = —NO$_2$<br>Y = CH$_3$OCH$_2$CH$_2$—O—C(=O)— | 44 | 40 | 120 |
| (2) X = CH$_3$OCH$_2$CH$_2$—O—C(=O)—<br>Y = —NO$_2$ | 20 | 20 | 70 |
| (3) X = —NO$_2$<br>Y = C$_2$H$_5$(OCH$_2$CH$_2$)$_2$—O—C(=O)— | 6 | 8 | 24 |
| (4) X = C$_2$H$_5$(OCH$_2$CH$_2$)$_2$—O—C(=O)—<br>Y = —NO$_2$ | 4 | 6 | 16 |
| (5) X = CH$_3$(OCH$_2$CH$_2$)$_3$—O—C(=O)—<br>Y = —NO$_2$ | 1 | 1.5 | 5 |
| (6) X = —NO$_2$<br>Y = CH$_3$(CH$_2$CH$_2$O—)$_{13.2}$—O—C(=O)— | soluble at any rate | soluble at any rate | soluble at any rate |
| comparative compound DNPO | 160 | 90 | 400 |

As R in

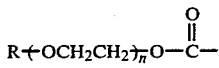

represented by X or Y of the compounds according to the present invention having the general foumula (I), mention may be made of lower alkyl groups such as a methyl group, an ethyl group, and a propyl group, and n may be any figure of 1–50, and preferably n=1, 2, or 3 or n÷4.1, 6.4, 8.7, 13.2, 22.3, 33.7 and 45.0 or figures near thereto attained when commercially available polyethylene glycols of the average molecular weights of 200, 300, 400, 600, 1000, 1500 and 2000, respectively. In addition, either one of X and Y may be a nitro group, and the other may be

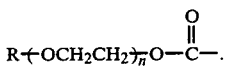

Now referring to the synthesizing method of the compounds according to the present invention, they can be easily obtained by by chlorinating o-(or p-)carboxy-p-(or o-)nitrophenol as a starting material with thionyl chloride, esterifying the resulting o-(or p-)chlorocarbonyl-p(or o-)nitrophenol with an alkylethylene glycol or an alkylpolyethylene glycol represented by R—OCH$_2$CH$_2$)$_n$OH to obtain o-(or p-)alkylethylene(or alkylpolyethylene)glycoxycarbonyl-p-(or o-)nitrophenol, and reacting the resultant with oxalyl chloride in the three reacting steps.

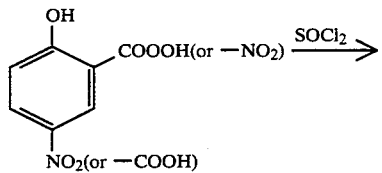

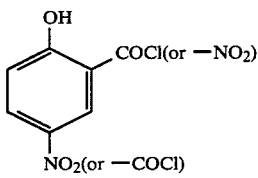

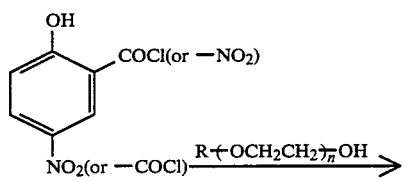

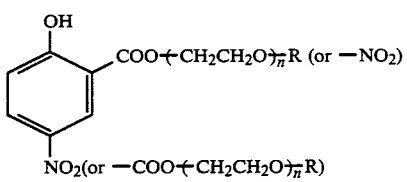

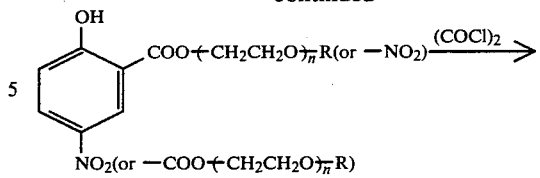

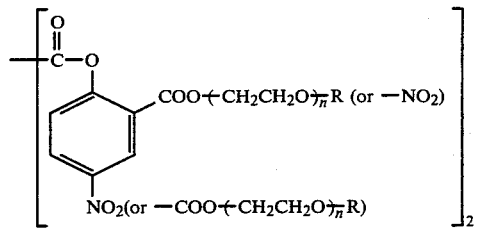

The above respective reacting steps are ordinarily carried out as follows:

For instance, when the chlorination in the first step is carried out by reacting o-(or p-)carboxy-p-(or o-)nitrophenol with thionyl chloride in a slightly excess amount thereto, preferably in the presence of an organic base such as pyridine, at an appropriate reaction temperature, for example, at 55°–60° C. by using a non-polar solvent such as benzene or toluene as a reaction solvent, the reaction is terminated in a few or several hours. Then, the reaction product is isolated in accordance with an ordinary manner through concentration under reduced pressure or the like to obtain o-(or p-)chlorocarbonyl-p-(or o-)nitrophenol. The esterification reaction in the second step is terminated in a few or several hours by reacting the o-(or p-)chlorocarbonyl-p-(or o-)nitrophenol obtained in the first step with an excess amount of alkylethylene glycol(or alkylpolyethylene glycol) at an appropriate reaction temperature, for instance, at 70°–80° C., and the resulting reaction product is isolated according to an ordinary manner through concentration under reduced pressure on the like to give o-(or p-)alkylethylene (or alkylpolyethylene)glycoxycarbonyl-p-(or o-)nitrophenol. The reaction with oxalyl chloride in the third step is terminated in a few or several hours by reacting the o-(or p-)alkylethylene(or alkylpolyethylene)glycoxycarbonyl-p-(or o-)nitrophenol with oxalyl chloride in an excess amount thereto, ordinarily in the presence of triethylamine in the same sample or so as the o-(or p-)alkylethylene(or alkylpolyethylene)gycoxycarbonyl-p-(or o-) nitrophenol, in an atmosphere of an inert gas at an appropriate reaction temperature, for instance, at 5°–45° C. with use of, for example, dry benzene as a reaction solvent, and precipitated triethylamine hydrochloric acid salt is isolated according to an ordinary manner through concentration under reduced pressure or the like to obtain an intended oxalic acid ester derivative. Moreover, to sum up, a pure product can be obtained in an ordinary way through treatment such as recrystallization, column chlomatography or the like.

The present invention is to provide the novel and more effective chemiluminescent substances for more highly sensitive detection of hydrogen peroxide or fluorescent substances in the method of measuring a very small amount of a component in a body fluid, or a component in a living body which component exhibits its physiological activity at a very small amount, and therefore the application range of the invention is extremely wide, thereby contributing to this technical field to an extremely large extent.

In the following, examples are shown, but they are merely illustrative of the invention and never interpreted to limit the scope thereof.

EXAMPLE 1

(1) 11 g (0.060 mol) of p-carboxy-o-nitrophenol, 50 ml of dry benzene, and five drops of pyridine were mixed together, to which 9.2 g (0.78 mol) of thionyl chloride was added dropwise under stirring at 50°–60° C. After the addition, the reaction was carried out at 55°–65° C. for 4 hours. Subsequent to the termination of the reaction, concentration was effected under reduced pressure to obtain 12 g of oil as a residue. Yield: 99.2%, IR(-Neat): 1750 cm$^{-1}$ assigned to

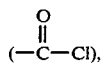

3250 cm$^{-1}$ assigned to ($>$OH)

(2) 2.5 g(0.0124 mol) of p-chlorocarbonyl-o-nitrophenol obtained as the oil in the reaction of the above first step was dissolved into 5 ml of diethylene glycol monoethyl ether, which was reacted at a reaction temperature of 70°–80° C. for 4 hours. After the termination of the reaction, a reaction solution was concentrated under reduced pressure to obtain 3.5 g of viscous oil. Yield: 94.3%, IR(Neat): 1725 cm$^{-1}$ assigned to

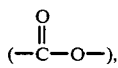

1150 cm$^{-1}$ assigned to

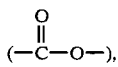

3250 cm$^{-1}$ assigned to ($>$OH). (3) 2 g (0.0067 mol) of p-(ethyldiethylene glycoxycarbonyl)-o-nitrophenol obtained as the viscous oil in the reaction of the above second step was dissolved into 20 ml of dry benzen, to which 0.7 g (0.0067 mol) of triethylamine was added. Then, 0.47 g (0.0037 mol) of oxalyl chloride was added thereto dropwise under cooling and stirring in an atmosphere of N$_2$ gas at 5°–6° C. After the addition, the reaction was carried out at room temperature for 3 hours. Subsequent to the termination of the reaction, precipitated triethylamine hydrochloric acid salt was filter off and then concentration was carried out under reduced pressure to obtain 2.0 g of an intended bis{p-(ethyldiethylene glycoxycarbonyl)-o-nitrophenyl} oxalate (hereinafter abbreviated as ECNPO) as light yellow crystals. Yield: 91.5%, m.p. 97°–99° C, IR(KBr): 1780 cm$^{-1}$ assigned to

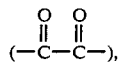

NMR (CDCl$_3$)δ: 1.2(6H, t, -CH$_2$CH$_3$), 3.6 (16H, m, -OCH$_2$-), 4.5 (4H, t, -COOCH$_2$-), 7.3–8.9 ppm(6H,m,ϕH), UV absorption(0.02 mM acetonitrile solution): λ$_{max}$ 232 nm, ε3.88×10$^4$, chemiluminescent test: positive.

Note: Chemiluminescent testing method

A-solution: 1 mg of perilene was dissolved into 100 ml of acetone.
B-solution: 0.01 mol acetone solution of H$_2$O$_2$-H$_2$O
C-solution: buffer solution of pH 4

A-solution, B-solution, and C-solution were mixed together each at an amount of 1 ml, and a sample was added thereto. A pale light was emitted in the dark.

EXAMPLE 2

(1) Except that 11 g of 5-nitrosalicylic acid was used instead of 11 g of p-carboxy-o-nitrophenol in the step (1) of Example 1, the reaction and the treatment were carried out in the same mannar as in the step (1) of Example 1 to obtain 11.8 g of o-chlorocarbonyl-p-nitrophenol (orange crystals). Yield: 97.6%.

(2) By using 2.5 g of the o-chlorocarbonyl-p-nitrophenol obtained in the above, the reaction and the treatment were carried out in the same manner as in the step (2) of Example 1 to obtain 3.6 g of o-(ethyldiethylene glycoxycarbonyl)-p-nitrophenol(yellow viscous oil). Yield: 96.8% (from an acid chloride).

(3) By using 2 g of the o-(ethyldiethylene glycoxycarbonyl)-p-nitrophenol obtained in the above, the reaction and the treatment were carried out in the same manner as in the step (3) of Example 1 to obtain 2.1 g of bis{o-(ethyldiethyeneglycoxycarbonyl)-p-nitrophenyl}oxalate as whitish crystals. Yield: 96.1%, m.p. 89°–90° C. IR(KBr): 1770 cm$^{-1}$ assigned to

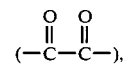

NMR(CDCl$_3$)δ: 1.2(6H, t, -CH$_2$CH$_3$), 3.6(16H, m, -OCH$_2$-), 4.5(4H, t, -COOCH$_2$-), 7.3–9.0 ppm(6H, m, ϕH), UV absorption(0.02 mM acetonitrile solution): λ$_{max}$ 221 nm, ε3.83×10$^4$, chemiluminescent test: positive.

EXAMPLE 3

(1) By using 11 g of p-carboxy-o-nitrophenol, the reaction and the treatment were carried out in the same manner as in the step (1) of Example 1 to obtain 12 g of p-chlorocarbonyl-o-nitophenol.

(2) 12 g(0.0595 mol) of the p-chlorocarbonyl-o-nitrophenol obtained in the above was dissolved into 22.8 g(0.3 mol) of ethylene glycol monomethyl ether, which was reacted at 70°–75° C. for 2 hours. After the reaction was terminated, the reaction liquid was concentrated under reduced pressure to remove an excess amount of ethylene glycol monomethyl ether to obtain 14.1 g of p-(methylethyleneglycoxycarbonyl)-o-nitrophenol (yellow crystals). Yield: 98.2%, m.p. 49°–51° C.

(3) 4.8 g(0.02 mol) of the p-(methylethylene glycoxycarbonyl)-o-nitrophenol obtained in the above and 2.2 g(0.022 mol) of triethyl amine were dissolved into 50 ml of dry benzene and 1.13 g(0.0089 mol) of oxalyl chloride was added thereto dropwise under cooling in an atmosphere of N$_2$ gas at 5°–8° C. After the addition, the reaction was carried out under stirring at room temperature for 4 hours. Subsequent to the reaction termination, precipitated crystals were collected through filtration, which was dissolved into 20-fold benzene under heating, and undissolved matters were filtered off at heating. Thereafter, the filtrate was concentrated up to a half thereof, and then precipitated crystals were collected under cooling through filtration to obtain 4.1 g of bis{p-(methylethylene glycoxycarbonyl)-o-nitrophenyl}oxalate (milky white crystals). Yield: 76.5%, m.p. 114°–116° C., IR(KBr): 1780 cm$^{-1}$ assigned to

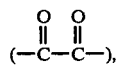

NMR(CDCl$_3$)δ: 3.4(6H, S, -OC$\underline{H}_3$), 3.7(4H, t, -C$\underline{H}_2$O-), 4.5(4H, t, -COOC$\underline{H}_2$-), 7.2–8.8 ppm(6H, m, φ$\underline{H}$), UV absorption (0.02 mM acetonitrile solution): λmax 233 nm, ε3.90×10$^4$, chemiluminescent test: positive.

EXAMPLE 4

(1) By using 11 g of 5-nitrosalicylic acid, the reaction and the treatment were carried out in the same manner as in the step (1) of Example 2 to obtain 12 g of o-chlorocarbonyl-p-nitrophenol.

(2) By using 12 g(0.0595 mol) of the o-chlorocarbonyl-p-nitrophenol obtained in the above instead of 12 g of the p-chlorocarbonyl-o-nitrophenol in the step (2) of Example 3, the reaction and the treatment were carried out in the same manner as in the step (2) of Example 3 to obtain 13.8 g of o-(methylethylene glycoxycarbonyl)-p-nitrophenol (yellow crystals). Yield: 96.2%, m.p. 67°–69° C.

(3) By using 4.8 g the o-(methylethylene glycoxycarbonyl)-p-nitrophenol obtained in the above instead of 4.8 g of the p-(methoxyethoxycarbonyl)-o-nitrophenol in the step (3) of Example 3, the reaction and the treatment were carried out in the same manner as in the step (3) of Example 3 to obtain 4.4 g of bis{o-(methylethylene glycoxycarbonyl)-p-nitrophenol}oxalate(white crystals). Yield: 82.1%, m.p. 126°–128° C., IR(KBr): 1770 cm$^{-1}$ assigned to

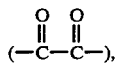

NMR(CDCl$_3$)δ: 3.3(6H, s, -OC$\underline{H}_3$), 3.7(4H, t, -C$\underline{H}_2$O-), 4.5(4H, t, -COOC$\underline{H}_2$-), 7.9–9.0 ppm (6H, m, φ$\underline{H}$), UV absorption (0.02 mM acetonitrile solution): λ$_{max}$ 222 nm, ε3.77×10$^4$, chemiluminescent test: positive.

EXAMPLE 5

(1) 61.8 g(0.1 mol) of monochloropolyethylene glycol which had been obtained by chlorinating polyethylene glycol 600 (the average molecular weight: 600) with thionyl chloride was dissolved into 50 ml of methanol, to which 28.9 g(0.15 mol) of 28% sodium methylate solution was poured. Then reaction was carried out under refluxing for 4 hours. Thereafter, methanol was distilled off, and 50 ml of dimethylsulfoxide was in turn poured to the residue, which was furthur reacted at 110°–120° C. for 3 hours. After the reaction, 150 ml of water was poured thereto, followed by extraction with 150 ml of chloroform, washing with water and drying through concentration to obtain 34.5 g of polyethylene glycol monomethyl ether as milky white waxy solid. Yield: 56.2% (from monochloropolyethylene glycol)

(2) By using 5.5 g of p-carboxy-o-nitrophenol, the reaction and the treatment were carried out in the same manner as in the step (1) of Example 1 to obtain 5.9 g of p-chlorocarbonyl-o-nitrophenol. Yield: 97.6%. (3) 22.1 g(0.036 mol) of the polyethylene glycol monomethyl ether obtained in the above (1) and 5.9 g(0.0293 mol) of the p-chlorocarbonyl-o-nitrophenol obtained in the above (2) were dissolved into 25 ml of dry benzene, which was reacted at 75°–80° C. for 5 hours. After the reaction, the reaction liquid was concentrated under reduced pressure to obtain 21.6 g of p-(methylpolyethylene glycoxycarbonyl)-o-nitrophenol as orange viscous oil. Yield: 94.6% (from acid chloride).

(4) 7.8 g(0.01 mol) of the p-(methylpolyethylene glycoxycarbonyl)-o-nitrophenol obtained in the above and 1.0 g(0.01 mol) of triethylamine were dissolved into 50 ml of dry benzene, to which 0.63 g(0.005 mol) of oxalyl chloride was added dropwise under cooling in an atmosphere of N$_2$ gas at 5°–10° C. After the addition, the reaction was carried out at room temperature for 4 hours. Thereafter, precipitated triethylamine hydrochloric acid salt was filtered off and the filtrate was concentrated under reduced pressure to obtain 7.1 g of bis{p-(methylpolyoxyethylene glycoxycarbonyl)-o-nitrophenyl}oxalate(n in -COO+CH$_2$CH$_2$O)$_{\overline{n}}$ CH$_3$ being about 13.2) as yellow viscous oil. Yield: 88.1%, IR(Neat): 1755 cm$^{-1}$ assigned to

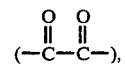

NMR(CDCl$_3$)δ: 3.4(6H, s, -OC$\underline{H}_3$), 3.65(102H, s, -OC$\underline{H}_2$-), 4.5(4H, t, -COOC$\underline{H}_2$-), 7.2–9.0 ppm(6H, m, φ$\underline{H}$), UV absorption(0.02 mM acetonitrile solution): λ$_{max}$ 237 nm, ε2.97×10$^4$, chemiluminescent test: positive

EXAMPLE 6

100 μl of a solution in which dansyl glycine was dissolved into 0.05M phthalic acid buffer solution (pH 4.0) to be at a concentration of 1 μM was sampled, to which 250 μl of 0.1M acetone solution of hydrogen peroxide and 100 μl of 0.83 mM ethyl acetate solution of ECNPO (or DNPO) were added in this order. Immediately thereafter, the intensity of chemiluminescence was measured every a specified time period by means of an ATP photometer (made by SAI Company in U.S.A.). Results obtained are shown in FIG. 1. On the other hand, changes in the relative chemiluminescent intensity every 10 minutes are shown in Table 2.

TABLE 2

| Change in the relative chemiluminescent intensity with lapse of time [Comparison between ECNPO (one of the compounds according to the present invention) and DNPO] | | | | |
|---|---|---|---|---|
| chemiluminescent reagent | lapse of time (sec) | | | |
| | 2 | 10 | 20 | 30 |
| ECNPO (present invention) | 80 | 65 | 49 | 36 |
| DNPO (comparative example) | 135 | 9 | (16 sec) 2.7 | — |

As obvious from FIG. 1 and Table 2, the apparent maximum chemiluminescent intensity is slightly smaller in ECNPO than in DNPO. However, while the intensity is extremely lowered with lapse of time in the case of DNPO, the degree of the intensity reduction is slightly smaller in the case of ECNPO. When the period of half-decay is calculated, DNPO has a short period of the half-decay of 3 seconds, whereas ECNPO exhibits an extremely long period of the half-decay of 27 seconds. That is, it is understood from the above that as compared with DNPO, ECNPO as the compound according to the present invention has an far longer chemiluminescent life and higher stabiblity. Similarly to DNPO, a known TCPO as a chemiluminescent reagent has the maximum chemiluminescent intensity of about one-tenth of the intensity of DNPO.

Furthermore, the above-mentioned measuring experiments were conducted with respect to both ECNPO and DNPO each at a concentration of 0.83 mM by using ethylacetate as a solvent of the chemiluminescent reagent. If the saturated solution of each of them is used, it goes without saying that the chemiluminescent intensity when ECNPO is used is naturally far larger than when DNPO is used, since the solubility of ECNPO ethyl acetate is about seventeen times as large as that of DNPO as shown in Table 1.

What is claimed is:

1. Oxalic acid ester derivatives represented by the general formula:

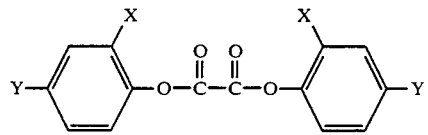

wherein either one of X and Y represents a nitro group, and the other represents

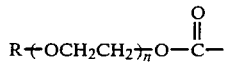

in which R represents a lower alkyl group, and n represents a figure of 1–50.

2. The derivatives claimed in claim 1, wherein X represents a nitro group, and Y represents

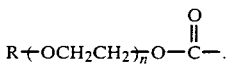

3. The derivatives claimed in claim 1, wherein X represents

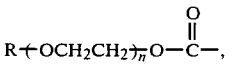

and Y represents a nitro group.

4. The derivatives claimed in claim 1, wherein n in the formula (I) represents 1–20.

5. The derivatives claimed in claim 1, wherein n in the formula (I) represents 1, 2 or 3.

6. The derivatives claimed in claim 1, which is bis{o-(methyltriethylene glycoxycarbonyl)-o-nitrophenyl}oxalate.

7. The derivatives claimed in claim 1, which is bis{p-(ethyldiethylene-glycoxycarbonyl)-o-nitrophenyl}oxalate.

8. The derivatives claimed in claim 1, which is bis{o-(ethyldiethylene glycoxycarbonyl)-p-nitrophenyl}oxalate.

9. The derivatives claimed in claim 1, which is bis{p-(methylethylene glycoxycarbonyl)-o-nitrophenyl}oxalate.

10. The derivatives claimed in claim 1, which is bis{o-(methylethylene glycoxycarbonyl)-p-nitrophenyl}oxalate.

11. The derivatives claimed in claim 1, which is bis{p-(methylpolyoxyethylene glycoxycarbonyl)-o-nitrophenyl}oxalate, provided that n in -COO-(-CH$_2$CH$_2$O-)$_n$CH$_3$ is about 13.2.

* * * * *